US008076136B2

(12) United States Patent
Clarke et al.

(10) Patent No.: US 8,076,136 B2
(45) Date of Patent: Dec. 13, 2011

(54) MINERALIZED THREE-DIMENSIONAL BONE CONSTRUCTS

(75) Inventors: Mark S. F. Clarke, Houston, TX (US); Alamelu Sundaresan, Sugarland, TX (US); Neal R. Pellis, Pearland, TX (US)

(73) Assignees: The United States of America as represented by the United States National Aeronautics and Space Administration, Washington, DC (US); University of Houston, Houston, TX (US); Universities Space Research Association, Columbia, MD (US)

( * ) Notice: Subject to any disclaimer, the term of this patent is extended or adjusted under 35 U.S.C. 154(b) by 701 days.

(21) Appl. No.: 11/693,662

(22) Filed: Mar. 29, 2007

(65) Prior Publication Data

US 2009/0061479 A1   Mar. 5, 2009

Related U.S. Application Data

(60) Provisional application No. 60/787,431, filed on Mar. 30, 2006.

(51) Int. Cl.
*C12N 5/07* (2010.01)
(52) U.S. Cl. ............... 435/373; 435/291.8; 435/325; 435/347; 435/377
(58) Field of Classification Search ............... 435/291.8, 435/325, 347, 373, 377
See application file for complete search history.

(56) References Cited

U.S. PATENT DOCUMENTS

| | | | |
|---|---|---|---|
| 4,988,623 A | 1/1991 | Schwarz et al. | |
| 5,026,650 A | 6/1991 | Schwarz et al. | |
| 5,153,151 A | 10/1992 | Aitken | |
| 5,155,034 A | 10/1992 | Wolf et al. | |
| 5,437,998 A | 8/1995 | Schwarz et al. | |
| 5,496,722 A | 3/1996 | Goodwin et al. | |
| 5,627,021 A | 5/1997 | Goodwin et al. | |
| 5,851,816 A | 12/1998 | Goodwin et al. | |
| 5,856,112 A | 1/1999 | Marley et al. | |
| 5,858,783 A | 1/1999 | Goodwin et al. | |
| 5,962,324 A | 10/1999 | O'Connor et al. | |
| 5,972,703 A * | 10/1999 | Long et al. | 435/372 |
| 6,001,642 A | 12/1999 | Tsao | |
| 6,107,081 A | 8/2000 | Feeback et al. | |
| 6,218,182 B1 | 4/2001 | Naughton et al. | |
| 6,406,711 B1 | 6/2002 | Lee et al. | |
| 6,537,589 B1 | 3/2003 | Chae et al. | |
| 6,773,713 B2 | 8/2004 | Bonassar et al. | |
| 6,811,776 B2 | 11/2004 | Kale et al. | |
| 6,844,187 B1 | 1/2005 | Wechsler et al. | |
| 6,998,264 B2 | 2/2006 | Ingram | |
| 2004/0058434 A1 | 3/2004 | Gault | |
| 2005/0002910 A1 | 1/2005 | Wolfinbarger et al. | |
| 2005/0229604 A1 | 10/2005 | Chen | |

OTHER PUBLICATIONS

Nakagawa et al. 2004. Osteoclastogenesis on Tissue-Engineered Bone. Tissue Engineering. 10:93-100.*
Salasznyk et al. 2004. Adhesion to Vitronectin and Collagen I Promotes Osteogenic Differentiation of Human Mesenchymal Stem Cells. J. Biomed. Biotech. 1:24-34.*
Yu et al. 2004. Bioreactor-based bone tissue engineering: The influence of dynamic flow on osteoblast phenotypic expression and matrix mineralization. PNAS 101(31):11203-11208.*
Meyers et al. 2004. Modeled Microgravity Disrupts Collagen I/Integrin Signaling During Osteoblastic Differentiation of Human Mesenchymal Stem Cells. Journal of Cellular Biochemistry 93:697-707.*
Klement et al. 2004. Skeletal tissue growth, differentiation and mineralization in the NASA Rotating Wall Vessel. Bone. 34:487-498.*
Nickerson et al., "Three-Dimensional Tissue Assemblies: Novel Models for Study of Salmonella Enterica Serovar Typhimurium Pathogenesis," *Infection & Immunity.* Nov. 2001, vol. 69(11), pp. 7106-7120.
Facer et al., "Rotary Culture Enhances Pre-Osteoblast Aggregation and Mineralization," *J. Dental Research* 2005, vol. 84 (6), pp. 542-547.
Carterson et al., "A549 Lung Epithelial Cells Grown as Three-Dimensional Aggregates: Alternative Tissue Culture Model for Pseudomonas Aeruginosa Pathogenesis," *Infection & Immunity.* Feb. 2005, vol. 73(2), pp. 1129-1140.

* cited by examiner

*Primary Examiner* — Taeyoon Kim
(74) *Attorney, Agent, or Firm* — Greenberg Traurig LLP

(57) ABSTRACT

The present disclosure provides ex vivo-derived mineralized three-dimensional bone constructs. The bone constructs are obtained by culturing osteoblasts and osteoclast precursors under randomized gravity vector conditions. Preferably, the randomized gravity vector conditions are obtained using a low shear stress rotating bioreactor, such as a High Aspect Ratio Vessel (HARV) culture system. The bone constructs of the disclosure have utility in physiological studies of bone formation and bone function, in drug discovery, and in orthopedics.

14 Claims, 7 Drawing Sheets

MINERALIZED THREE-DIMENSIONAL BONE CONSTRUCTS

This application claims the benefit of U.S. Provisional Patent Application Ser. No. 60/787,431, filed Mar. 30, 2006, specifically incorporated herein by reference in its entirety.

The U.S. Government has a paid-up license in this invention and the right in limited circumstances to require the patent owners to license others on reasonable terms as provided for by the terms of Contract No. NNJ04HF46H awarded by the National Aeronautics and Space Administration (NASA).

FIELD OF THE INVENTION

The invention relates to ex vivo-derived mineralized three-dimensional bone constructs which replicate natural bone.

BACKGROUND

One of the central problems associated with studying both the normal and pathophysiology of bone is that as an organ system it is slow growing and the time to show an observable response to a particular stimulus is relatively long. The nature of the mineralized tissue matrix of bone in vivo and its complex architecture also presents several technical problems associated with how experimental observations can be made. At present, truly informative studies designed to understand bone physiology have relied primarily on the removal of samples of bone tissue from normal or diseased tissue either in a clinical setting or from experimental animal models.

To date, there is no three dimensional tissue culture model of bone, either of animal or human origin. The prior art has relied primarily on the use of monotype cell type cultures of osteoblasts or osteoclast cells grown on planar, two dimensional tissue culture surfaces. Such cultures have also been grown in three dimensional collagen support gels and some investigators have utilized culture systems that allow types of mechanical strain to be applied to the cells in order to study the effects of mechanical loading. However, these cultures have been primarily focused on the responses of a single cell type, such as osteoblasts, to various environmental stimuli.

Existing planar monotype tissue culture models of bone do not allow the study of the interactions between the different cell types present in normal bone responsible for normal bone remodeling. The developmentally inactive osteocyte cell type present in the mineralized matrix of normal bone in vivo (from which osteoblasts are derived) have yet to be fully characterized in any tissue culture model due to their supposed transformation into osteoblasts once they have been removed from the bone matrix and placed into culture.

Moreover, the process of mineralization, which is essential to the formation of new bone, has previously only been studied in monotype cultures of osteoblasts. The mineralization process has been studied in such models in the absence of the major cell type involved in the removal of mineralized material, namely the osteoclast. However, the complex interplay between both of these cell types is essential for normal bone remodeling (i.e. bone formation and bone loss). Without both cell types being present, a true in vitro/ex vivo representation of the normal or indeed pathological processes involved in the bone remodeling process is impossible. As such, the use of such monotype culture models to investigate the effects of manipulations, such as anti-osteoporetic drugs or mechanical load interventions, have limited utility due to the lack of similarity to the true physiological state existing within bone tissue in vivo.

SUMMARY

In one aspect, the disclosure provides ex vivo-derived mineralized three-dimensional bone constructs, each comprising a spheroid of between about 200 μm and about 4 mm in diameter having an outer layer surrounding an inner core. The outer layer is comprised of osteoclasts, and the inner layer is comprised of osteoblasts, osteocytes, or both osteoblasts and osteocytes embedded within a crystalline matrix. The crystalline matrix is comprised of calcium, phosphates, and carbonates.

In another aspect, the disclosure provides methods for producing mineralized three-dimensional bone constructs. In one embodiment, a method comprises introducing osteoclast precursors and osteoblasts into a culture vessel comprising a matrix-free culture medium; culturing the osteoclast precursors and the osteoblasts under randomized gravity vector conditions wherein aggregates of the osteoblasts and the osteoclast precursors are formed; and introducing a matrix-free mineralization culture medium into the culture vessel and culturing the aggregates under randomized gravity vector conditions.

In another embodiment, a method comprises culturing osteoclast precursors and osteoblasts in a matrix-free culture medium using a low shear rotational three-dimensional tissue culture technique under conditions effective to form aggregates comprising the osteoblasts and the osteoclast precursors, and culturing the aggregates using said low shear rotational three-dimensional tissue culture technique in a matrix-free mineralization culture medium that promotes mineralization of said aggregates.

In another embodiment, a method comprises introducing osteoclast precursors and osteoblasts into a cylindrical culture vessel that rotates about a substantially central horizontal axis, the cylindrical culture vessel comprising a matrix-free culture medium; culturing the osteoblasts and the osteoclast precursors in the cylindrical culture vessel during substantially horizontal rotation at a rate effective to create low shear conditions and to promote the formation of aggregates comprising the osteoclast precursors and said osteoblasts; and introducing a matrix-free mineralization culture medium into the cylindrical culture vessel and culturing the aggregates during substantially horizontal rotation at a rate effective to create low shear conditions.

In another embodiment, the method comprises introducing osteoclast precursors and osteoblasts into a cylindrical culture vessel that rotates about a substantially central horizontal axis, the cylindrical culture vessel comprising a matrix-free culture medium; culturing the osteoblasts and the osteoclast precursors in the cylindrical culture vessel during substantially horizontal rotation at a rate effective to create low shear conditions and to promote the formation of aggregates comprising the osteoclast precursors and said osteoblasts; further culturing the aggregates in the cylindrical culture vessel during substantially horizontal rotation at a rate effective to create low shear conditions so that the aggregates grow in size and the osteoclast precursors differentiate into osteoclasts; and introducing a matrix-free mineralization culture medium into the cylindrical culture vessel and culturing the aggregates during substantially horizontal rotation at a rate effective to create low shear conditions, wherein the mineralized three-dimensional bone constructs are formed.

In another aspect, the disclosure provides a mineralized three-dimensional bone construct produced by introducing osteoclast precursors and osteoblasts into a cylindrical culture vessel that rotates about a substantially central horizontal axis, the cylindrical culture vessel comprising a matrix-free culture medium; culturing the osteoblasts and the osteoclast precursors in the cylindrical culture vessel during substantially horizontal rotation at a rate effective to create low shear conditions and to promote the formation of aggregates comprising the osteoclast precursors and said osteoblasts; further culturing the aggregates in the cylindrical culture vessel during substantially horizontal rotation at a rate effective to create low shear conditions so that the aggregates grow in size and the osteoclast precursors differentiate into osteoclasts; and introducing a matrix-free mineralization culture medium into the cylindrical culture vessel and culturing the aggregates during substantially horizontal rotation at a rate effective to create low shear conditions, wherein the mineralized three-dimensional bone constructs are formed.

BRIEF DESCRIPTION OF THE DRAWINGS

FIG. 3A presents a fluorescence confocal microscopy image of an optical section through bone constructs in which the osteoclast precursor cells were labeled with a fluorescent cell tracking dye (observable as white spots in FIG. 3A). FIG. 3B shows the same constructs viewed in incident laser light (i.e. non-fluorescent illumination) to illustrate the shape of the constructs. The scale bar in each of FIG. 3A and FIG. 3B is 200 μm.

FIG. 5A shows a 5× magnification image of Alizarin red S staining and FIG. 5B shows a 20× magnification image of Alizarin red S staining (which appears as the dark regions of the images). FIG. 5C shows a 5× magnification image of von Kossa staining and FIG. 5B shows a 20× magnification image of von Kossa staining (which appears as the dark regions of the images).

FIG. 6A is a 5× magnification image and FIG. 6B is a 20× magnification image. The dark regions of the image indicate staining. Arrows in FIG. 6B point to large numbers of cells embedded within the crystalline matrix in the three dimensional construct.

FIG. 7A shows osteocalcein staining, FIG. 7B shows CellTracker-Orange staining, and FIG. 7C shows the same construct illuminated with incident laser light. The results indicate that osteocalcein staining and cell tracking dye (both visible as a white "ring" around the construct in FIGS. 7A and 7B) are spatially localized to the same area of the construct.

DETAILED DESCRIPTION

Figure 1:
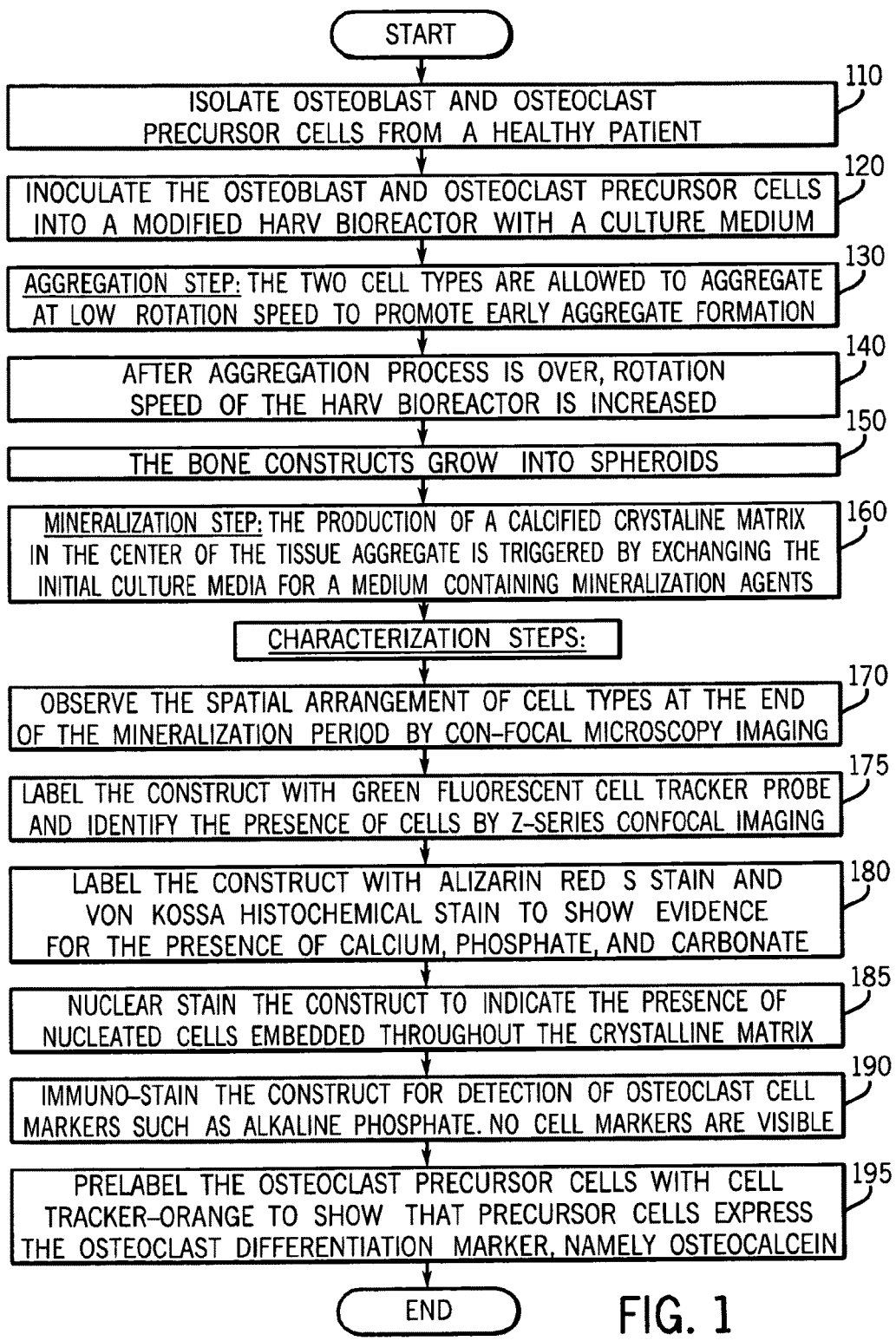
FIG. 1 is a flowchart of an example of a method for preparing mineralized three-dimensional bone constructs.

In one aspect, the present disclosure provides mineralized three-dimensional bone constructs (sometimes referred to herein simply as "bone constructs"). The mineralized three dimensional constructs of the disclosure are "bone like" in appearance by visual inspection, in certain important respects resembling trabecular bone (also known in the art as "spongy bone"). In preferred embodiments, the mineralized three-dimensional bone constructs of the disclosure are macroscopic in size and are approximately spheroidal in shape, preferably between about 200 μm and about 4 mm in diameter; however, larger and smaller bone constructs are specifically contemplated.

The bone constructs comprise an inner core surrounded by an outer layer. The inner core comprises a three-dimensional crystalline matrix that stains positively with Alizarin Red S stain and with the von Kossa histochemical stain, indicating that it comprises mineral elements observed in normal human bone in vivo, including calcium, phosphates, and carbonates. The inner core also comprises osteoblasts and/or osteocytes embedded within the crystalline matrix, and is preferably devoid of necrotic tissue. Osteocytes are developmentally inactive cells found only in native bone tissue in vivo and are believed to be formed from osteoblasts that have become trapped in the crystalline matrix. The outer layer is comprised of osteoclasts, which may express the differentiation marker osteocalcein. The cell types in the bone constructs of the disclosure can be obtained from any mammalian species, but are preferably obtained from humans.

In another aspect, the disclosure provides methods for producing the mineralized three-dimensional bone constructs. In general, the bone constructs of the disclosure are produced by culturing osteoclast precursors and osteoblasts together under randomized gravity vector conditions (approaching those conditions that cultured cells experience during microgravity culture) in a matrix-free culture medium. Osteoclast precursors may be obtained from bone marrow and/or peripheral blood lymphocytes by techniques well known in the art. Osteoclast precursors may also be obtained from commercial sources (for example, from Cambrex/Lonza, Inc.). Osteoblasts, preferably primary human osteoblasts, may also be obtained by techniques well known in the art, and may also be obtained from commercial sources (for example, from PromoCell, Inc. and from Cambrex/Lonza, Inc.). A "matrix-free culture medium" is a cell culture medium which does not include carrier material (such as microcarrier beads or collagen gels) onto which osteoblasts and osteoclast precursors can attach. Suitable cell culture media include Eagle's Minimal Essential Medium (EMEM) or Dulbecco's Modified Eagle's Medium (DMEM), preferably supplemented with fetal bovine serum (FBS). Preferably, the matrix-free culture medium also comprises osteoblast growth supplements such as ascorbic acid. The matrix-free culture medium preferably also further comprises osteoclast differentiation factors, such as Receptor Activator of NF-kB (RANK) ligand and macrophage colony stimulating factor (M-CSF). For example, in one embodiment the matrix-free culture medium comprises FBS-supplemented DMEM, ascorbic acid, RANK ligand, and M-CSF. Example 2 includes a description of one suitable matrix-free culture medium.

The osteoclast precursors and the osteoblasts are cultured together under randomized gravity vector conditions effective to achieve the formation of mixed aggregates of the two cell types. The aggregates are then further cultured under randomized gravity vector conditions to increase the aggregates size and to differentiate the osteoclast precursors into mature osteoclasts.

After a predetermined time, the aggregates are cultured under randomized gravity vector conditions in a matrix-free mineralization culture medium. A "matrix-free mineralization culture medium" is a cell culture medium that includes one or more mineralization agents, such as osteoblast differentiation factors, that induce osteoblasts to produce crystalline deposits (comprising calcium, phosphate, and carbonates) but which does not include carrier material (such as microcarrier beads and collagen gels) onto which osteoblasts and osteoclast precursors can attach. For example, in one embodiment, a matrix-free mineralization culture medium comprises FBS-supplemented EMEM or DMEM, supplemented with the osteoblast differentiation factors. Osteoblast differentiation factors include beta-glycerophosphate and hydrocortisone-21-hemisuccinate. Preferably, the matrix-free mineralization culture medium also includes osteoclast differentiation factors such as RANK ligand and M-CSF, and also includes osteoblast growth supplements such as ascorbic acid. For example, in one embodiment the matrix-free mineralization culture medium comprises FBS-supplemented DMEM, beta-glycerophosphate, ascorbic acid, hydrocortisone-21-hemisuccinate, RANK ligand and M-CSF. Example 2 includes a description of one suitable matrix-free mineralization medium.

In preferred embodiments, randomized gravity vector conditions are obtained by culturing osteoclast precursors and osteoblasts in a low shear stress rotating bioreactor. Such bioreactors were initially designed to mimic some of the physical conditions experienced by cells cultured in true microgravity during space flight. In general, a low shear stress rotating bioreactor comprises a cylindrical culture vessel. One or more ports are operatively associated with the lumen of the vessel for the introduction and removal of cells and culture media. The cylindrical culture vessel is completely filled with a culture medium to eliminate head space. The cylindrical culture vessel rotates about a substantially central horizontal axis. The resulting substantially horizontal rotation occurs at a rate chosen so that (1) there is essentially no relative motion between the walls of the vessel and the culture medium; and (2) cells remain in suspension within a determined spatial region of the vessel such that they experience a continuous "free fall" through the culture medium at terminal velocity with low shear stress and low turbulence. This free fall state may be maintained continuously for up to several months in some applications described in the prior art. The continuous orbital movement of the medium relative to the cells also allows for highly efficient transfer of gases and nutrients.

In some embodiments, the diameter of the cylindrical culture vessel is substantially greater than its height. Such cylindrical culture vessels are often referred to in the art as High Aspect Ratio Vessels (HARVs). For example, a HARV having a volume of 10 mL may have a diameter of about 10 cm and a height of about 1 cm. At least a portion of the vessel walls may be comprised of a gas permeable membrane to allow gas exchange between the culture medium and the surrounding incubator environment. A suitable HARV is described in, for example, U.S. Pat. No. 5,437,998, incorporated by reference herein in its entirety. One commercial embodiment of a HARV is the Rotating Cell Culture System (RCCS) available from Synthecon, Inc.

In some embodiments, the diameter of the cylindrical culture vessel is substantially smaller than its height. Such cylindrical culture vessels are often referred to in the art as Slow Turning Lateral Vessels (STLVs). STLVs typically have a core, comprised of a gas permeable membrane, running through the center of the cylinder in order to allow gas exchange between the culture medium and the surrounding incubator environment. STLVs are available from Synthecon, Inc.

The use of low shear stressing rotating bioreactor culture systems is described in, for example, Nickerson et al., Immunity. 69:7106-7120 (2001); Carterson et al., Infection & Immunity. 73(2): 1129-40 (2005); and in Goodwin et al. U.S. Pat. No. 5,496,722, each of which is specifically incorporated herein by reference in its entirety.

In one embodiment, osteoclast precursors and osteoblasts are introduced into a cylindrical culture vessel in matrix-free culture medium. The osteoclast precursors and the osteoblasts may be introduced into the cylindrical culture vessel separately, or they may be introduced into the cylindrical culture vessel as a pre-mixture of the two cell types. Preferably, the cells are introduced into the cylindrical culture vessel at a osteoblast:osteoclast precursor ratio of from about 2:1 to about 3:1, although higher and lower ratios are within the scope of the disclosure. The absolute number of cells introduced into the cylindrical culture vessel may also be varied. For example, in some embodiments where a ratio of about 2:1 is employed, about 2 million osteoblasts and about 1 million osteoclast precursors are introduced; in other embodiments about 4 million osteoblasts and about 2 million osteoclast precursors are introduced; and in still further embodiments about 8 million osteoblasts and about 4 million osteoclast precursors are introduced. The ratio of osteoblasts:osteoclast precursors and the absolute number of cells can be varied in order to vary the size and the number of aggregates formed. In addition, other cell types may also be introduced into the cylindrical culture vessel. For example, bone marrow stroma and stem cells may be cultured along with the osteoblasts and the osteoclast precursors.

One or more cell types may optionally be labeled with a cell-tracking marker, such as a fluorescent cell-tracking dye, prior to their introduction into the cylindrical culture vessel. In this way, it is possible to determine the location of the individual cell types during, or at the conclusion of, the formation of the bone constructs. For example, fluorescent Cell-Tracker dyes, available from Invitrogen, Inc., may be used in conjunction with fluorescence microscopy techniques, such as confocal fluorescence microscopy. If more than one cell type is labeled, then they are labeled with different colored dyes so that each cell type can be tracked independently.

Cells are then cultured in the matrix-free culture medium in the cylindrical culture vessel during substantially horizontal rotation to form aggregates of the two cell types. The rate of substantially horizontal rotation during the aggregation phase is chosen so that both (1) low shear conditions are obtained; and (2) the osteoclast precursors and the osteoblasts are able to coalesce and form aggregates. The rate of substantially horizontal rotation may be selected by monitoring the cylindrical culture vessel and by monitoring the cells and aggregates in the cylindrical culture vessel (for example using microscopy), to insure that the cells and aggregates are not sedimenting (which may be caused by too low a rate of rotation) or experiencing mechanical or excessive hydrodynamic shear stress. In embodiments in which a HARV is used, osteoclast precursors and osteoblasts may form a "boundary" layer situated in the middle of the HARV during the aggregation phase.

Preferably, the rate of substantially horizontal rotation during the aggregation phase is lower than the rate typically used for culturing cells. For example, in embodiments where the cylindrical culture vessel is a 10 mL HARV having a diameter of about 10 cm and a height of about 1 cm, substantially horizontal rotation at less than about 14 revolutions per minute (rpm) may be used. More preferably, substantially horizontal rotation at less than about 12 rpm is used. In certain preferred embodiments, substantially horizontal rotation at between about 1 rpm and about 4 rpm is used. In one specific embodiment, substantially horizontal rotation at about 2 rpm is used. Note that the aforementioned rpm values are provided with reference to a 10 mL HARV having the aforementioned dimensions. The rpm values will vary depending on the volume and dimensions of the cylindrical culture vessel. The rpm values during the aggregation phase for all such vessels are easily determined using the aforementioned methodology.

Without being bound by a particular theory or mechanism, it is believed that the use of a matrix-free culture medium allows the use of rates of rotation that are substantially lower than previously reported in the art for culturing mammalian cells in a low shear stress rotating bioreactor. The use of low rotation rates, in turn, is believed for the first time to promote efficient association of osteoclast precursors and osteoblasts into aggregates, and to promote three-dimensional organization of these two cell types within the aggregates. Thus, the organization of the cell types within the aggregate is not constrained or influenced by an exogenous carrier material, but rather by native cell-cell interaction. Consequently, the three-dimensional organization of the osteoblasts and osteoclasts is physiologically realistic.

The rate of substantially horizontal rotation may optionally be adjusted periodically during the aggregation phase in order to compensate for the increase in the sedimentation velocity (which is a function of volume and density) of the forming aggregates, thereby maintaining the aggregates in low shear "free fall" and preventing impact with the vessel wall.

The aggregation phase proceeds for a period of time sufficient to produce the desired size of aggregates. Aggregate formation may be monitored during the aggregation phase by visual inspection, including through the use of microscopy. It will be apparent from the disclosure that the size of the aggregates is also dependent on the number of cells that are initially introduced into the cylindrical culture vessel, the length of time allowed for aggregation, as well as the rotation rate. In one example, the aggregation phase is allowed to proceed for between about 24 hours and about 48 hours.

Once aggregates of the desired size have formed, the aggregates are preferably further cultured in the cylindrical culture vessel during substantially horizontal rotation for a period of time sufficient to allow the aggregates to grow to a desired size through cell proliferation and/or to allow the osteoclast precursors in the aggregates to differentiate into osteoclasts. For example, the further culturing of the aggregates may proceed for between about 5 and about 7 days and may lead to grown aggregates having a diameter from between about 200 µm and about 4 mm. The resultant aggregates are sometimes referred to herein as "spheroids." Preferably, the rate of substantially horizontal rotation during the further culturing is higher than the rate during the aggregation phase, but still provides low shear conditions in the cylindrical culture vessel. For example, a rotation rate of between about 9 rpm and about 16 rpm, preferably about 14 rpm, may be used during further culturing for the 10 mL HARV exemplified above. The rate of substantially horizontal rotation may optionally be adjusted periodically during the further culturing phase in order to compensate for the increase in the sedimentation pathway of the aggregates as they grow in size (and hence undergo changes in volume and density), thereby maintaining the growing aggregates in low shear "free fall" and preventing impact with the vessel wall.

Once aggregates have attained a desired size, a matrix-free mineralization culture medium is introduced into the cylindrical culture vessel and the aggregates are cultured during substantially horizontal rotation until they become mineralized, thereby forming the mineralized three-dimensional bone constructs of the disclosure. For example, the mineralization process may proceed for between about 7 days and about 21 days. Preferably, the rate of substantially horizontal rotation during such the mineralization process is higher than the rate during the aggregation phase, but still provides low shear conditions in the cylindrical culture vessel. For example, a rotation rate of between about 9 rpm and about 20 rpm, preferably about 14 rpm, may be used during the mineralization phase for the 10 mL HARV exemplified above. The rate of substantially horizontal rotation may optionally be adjusted periodically during the mineralization phase in order to compensate for the increase in the sedimentation pathway of the aggregates as they increase in mass, thereby maintaining the mineralizing aggregates in low shear "free fall" and preventing impact with the vessel walls.

Mineralized three-dimensional bone constructs are harvested once they have achieved the desired size and mass. In cylindrical culture vessels with one or more access ports, the bone constructs are removed through a part. When the bone constructs exceed the diameter of the port, the vessel is disassembled to remove the bone constructs.

Osteoclasts and osteoblasts act coordinately in the mineralization process that occurs in vivo during bone formation and bone restructuring. Accordingly, the mineralized three-dimensional bone constructs of the disclosure, formed by the coordinated activity of osteoblasts and osteoclasts, are physiologically realistic.

As described above, the mineralized three-dimensional bone constructs of the disclosure mimic trabecular bone in many important aspects. The bone constructs of the disclosure therefore have a great many uses in the fields of, for example, physiology research and development, pharmaceutical research, and orthopedics. Without limitation, these include the direct benefit of developing a model for studying both normal bone physiology and the pathological responses observed in disease states such as osteoporosis, as well as providing a highly economical platform for drug development as it relates to the treatment of bone diseases.

The bone constructs of the disclosure also can be used for autologous grafts. Specifically, diseased or missing bone may be replaced with ex-vivo-derived mineralized three-dimensional bone constructs in which the component osteoclasts and osteoblasts are harvested from healthy bone and peripheral blood lymphocytes of the patient requiring the bone graft. Examples of pathologies where the bone constructs of the disclosure have therapeutic utility include fractures, non-unions of fractures, congenital deformities of bone, bone infections, bone loss, segmental bone defects, bone tumors, metabolic and endocrine disorders affecting bone, and tooth loss.

The bone constructs of the disclosure can also be used for allogenic (allograft) grafts. Specifically, diseased or missing bone can be replaced with ex vivo-derived mineralized three-dimensional bone constructs in which the component osteoclasts and osteoblasts are harvested from healthy bone and peripheral blood lymphocytes of another donor for the benefit of a patient requiring bone graft. Examples of pathologies where the bone constructs of the disclosure have therapeutic utility include fractures, non-unions of fractures, congenital deformities of bone, bone infections, bone loss, segmental bone defects, bone tumors, metabolic and endocrine disorders affecting bone, and tooth loss.

Because the bone constructs of the disclosure closely resemble bone formed in vivo, it is expected that they produce unique factors and/or cytokines essential for bone remodeling. Accordingly, the bone constructs of the disclosure serve as a source for identification and harvesting of these factors.

The bone constructs of the disclosure may also be used to study the interface between prosthetic devices/materials and bone tissue.

Sensors or stimulation devices may be incorporated into the bone constructs of the disclosure, and the resulting constructs implanted into bone tissue in vivo.

The bone constructs of the disclosure also may be used in the production of large structures of specific dimensions for "form-fitted" applications such as replacement of large regions of the skeleton. This may be achieved using a combination of tissue scaffolding/synthetic support materials embedded with numerous bone constructs to generate a much larger composite tissue aggregate.

The bone constructs of the disclosure also provide a low cost alternative in which to study the effects of microgravity, and of other space environment insults, such as radiation, on the process of bone formation/bone loss.

The following examples are not to be construed as limiting the scope of the invention disclosed herein in any way.

EXAMPLES

Example 1

Flow Chart of a Method For Producing Bone Constructs

A flow chart of the method for producing mineralized three-dimensional bone constructs is provided in FIG. 1. Osteoblast and osteoclast precursor cells are first isolated (110) from a healthy patient and then inoculated (120) into a modified High Aspect Rotating Vessel (HARV) with a matrix-free culture medium. Cells are allowed to aggregate (130) at a rotation speed (typically 2 rpm) much lower than that commonly used for the culture of mammalian cells. Low speed promotes aggregation of the two or more cell types in the early stages of aggregate formation. After the aggregation period is over, the rotation speed of the High Aspect Rotating Vessel is increased (140). This allows the bone construct to grow into spheroids (150) in a state of "free fall". The mineralization step (160) is then initiated by exchanging the initial matrix-free culture medium for a matrix-free mineralization culture medium, which initiates the production of a calcified crystalline matrix in the center of the tissue aggregate. The bone constructs are then characterized. The spatial arrangement of the different cell types is observed by confocal microscopy imaging (170). The cells are visualized with Z-series confocal imaging (175) by pre-labeling the initial cell constituents of the construct with green fluorescent cell tracker probe. The presence of calcium, phosphate and carbonate is revealed by using Alizarin red S stain and Kossa histochemical stain (180), while the presence of nucleated cells embedded in the crystalline matrix is revealed by nuclear staining (185). Immuno-staining of the construct (190) shows that cell markers such as alkaline phosphatase are absent from the cells embedded in the crystalline matrix. Finally, prelabeling of the osteoclast precursor cells with Cell Tracker-Orange (195) shows that precursor cells allowed to aggregate and organize under these culture conditions express the osteoclast differentiation marker, namely osteocalcein.

Example 2

Production of Bone Constructs In A HARV

Cryopreserved primary normal human osteoblast cells and normal human osteoclast precursor cells were purchased from the Cambrex Corporation (East Rutherford, N.J.) and stored frozen under liquid nitrogen until needed.

Osteoblast cells were rapidly thawed by placing the vial in a 37° C. oven, removing the cell suspension from the vial and placing it in a 15 ml centrifugation tube and then diluting the cell suspension with 10 ml of Dulbecco's Modified Essential Medium (DMEM) supplemented with 10% (v/v) fetal bovine serum (10% FBS-DMEM). The cells were then collected by centrifugation at 100×g for 5 min at 4° C. The supernatant was then removed and the cell pellet was resuspended by gentle tituration in 10 ml of fresh 10% FBS-DMEM supplemented with 5 µM ascorbic acid and 1 mg/ml GA-1000 (gentamicin/amphotericin B mixture). This process was carried out to wash away the cryopreservatives in which the osteoblast cells had been frozen.

The resulting cell suspension was then inoculated into a T-75 tissue culture flask and incubated at 37° C. in a 5% $CO_2$ atmosphere tissue culture incubator for a total period of seven days, with the medium being exchanged every three days. After seven days the osteoblast culture was approaching confluence and the osteoblast cells were harvested by removing the cells from the surface of the flask using trypsin/EDTA digestion followed by collection of the cells by centrifugation as above. The cell pellet was then gently resuspended in 20 ml of fresh 10% FBS-DMEM supplemented with 5 µM ascorbic acid and 1 mg/ml GA-1000. The resulting cell suspension was then inoculated into two T-75 tissue culture flasks and again cultured for an additional seven days. This process of osteoblast cell expansion continued until the cells had reached passage 5 (i.e. five expansion/population doubling cycles).

When the osteoblast cells had reached Passage 5 in culture they were harvested using trypsin/EDTA digestion followed by collection of the cells by centrifugation as above. The cell pellet was then gently resuspended in 10 ml of fresh 10% FBS-DMEM supplemented with 5 µM ascorbic acid, 100 U/ml penicillin and 100 ug/ml streptomycin, penicillin/streptomycin being substituted for GA-1000 at this point due to the potential negative effects of gentamicin on the capability of osteoblast cells to produce mineralized extracellular matrix. The resulting osteoblast cell suspension was counted using a hemacytometer to ascertain the number of osteoblast cells/ml. An aliquot of cell suspension containing a total of six million osteoblast cells was removed and placed in a separate 15 ml centrifugation tube in preparation for the addition of osteoclast precursor cells.

Osteoclast precursor cells were rapidly thawed by placing the vial in a 37° C. oven, removing the cell suspension from the vial and placing it in a 15 ml centrifugation tube and then diluting the cell suspension with 10 ml of Dulbecco's Modified Essential Medium (DMEM) supplemented with 10% (v/v) fetal bovine serum (10% FBS-DMEM). The cells were then collected by centrifugation at 100×g for 5 min at 4° C. The supernatant was then removed and the cell pellet was resuspended by gentle tituration in 1 ml of fresh 10% FBS-DMEM supplemented with 5 µM ascorbic acid, 100 U/ml penicillin and 100 ug/ml streptomycin. This process was carried out to wash away the cryopreservatives in which the osteoclast cells had been frozen.

The resulting osteoclast precursor cell suspension was counted using a hemacytometer to ascertain the number of osteoclast precursor cells/ml. An aliquot of cell suspension containing a total of two million osteoclast cells was removed and added to the 15 ml centrifuge tube containing the six million osteoblast cells. The volume of medium in the centrifuge tube was then was adjusted to a total of 10 ml by the addition of fresh 10% FBS-DMEM supplemented with 5 µM ascorbic acid, 100 U/ml penicillin and 100 ug/ml streptomycin. Finally, the 10 ml of medium containing both osteoblast and osteoclast cells was supplemented with 50 ng/ml macrophage colony stimulating factor (M-CSF) and 50 ng/ml of receptor activator of NF-kB (RANK) ligand.

The resulting osteoblast/osteoclast cell suspension was then inoculated into a 10 ml rotating cell culture system (RCCS) flask (also know as a High Aspect Ratio Vessel—HARV) (Synthecon, Inc.) and horizontally rotated at 2 RPM for a period of 24 hr to allow coalescence of the osteoblast and osteoclast cells into a solid, three dimensional tissue construct. After a period of 24 hr, the rotation speed of the HARV was increased to 14 RPM in order ensure that the tissue construct was maintained in an optimal position within the HARV, namely not touching or hitting the sides of the rotating HARV rather in a state of "free-fall" within the medium contained within the rotating HARV. The cell medium within the HARV was exchanged with 10 ml of fresh 10% FBS-DMEM supplemented with 5 µM ascorbic acid, 100 U/ml penicillin, 100 ug/ml streptomycin, 50 ng/ml macrophage colony stimulating factor (M-CSF) and 50 ng/ml of receptor activator of NF-kB (RANK) ligand (a matrix-free culture medium) after every fourth day of culture.

After a period of seven days of culture in the HARV under the above conditions the medium was exchanged for 10 ml of fresh 10% FBS-DMEM supplemented with 5 µM ascorbic acid, 100 U/ml penicillin, 100 ug/ml streptomycin, 50 ng/ml macrophage colony stimulating factor (M-CSF), 50 ng/ml of receptor activator of NF-kB (RANK) ligand, 200 µM hydrocortisone-21-hemisuccinate and 10 mM beta-glycerophosphate (a matrix-free mineralization culture medium). The hydrocortisone-21-hemisuccinate and beta-glycerophosphate were added to the medium to induce mineralization of the tissue construct by the osteoblasts. The cell medium within the HARV was exchanged with 10 ml of fresh 10% FBS-DMEM supplemented with 5 µM ascorbic acid, 100 U/ml penicillin, 100 ug/ml streptomycin, 50 ng/ml macrophage colony stimulating factor (M-CSF), 50 ng/ml of receptor activator of NF-kB (RANK) ligand, 200 µM hydrocortisone-21-hemisuccinate and 10 mM beta-glycerophosphate every fourth day until the tissue construct was harvested.

Example 3

Imaging of Bone Constructs

Figure 2A:
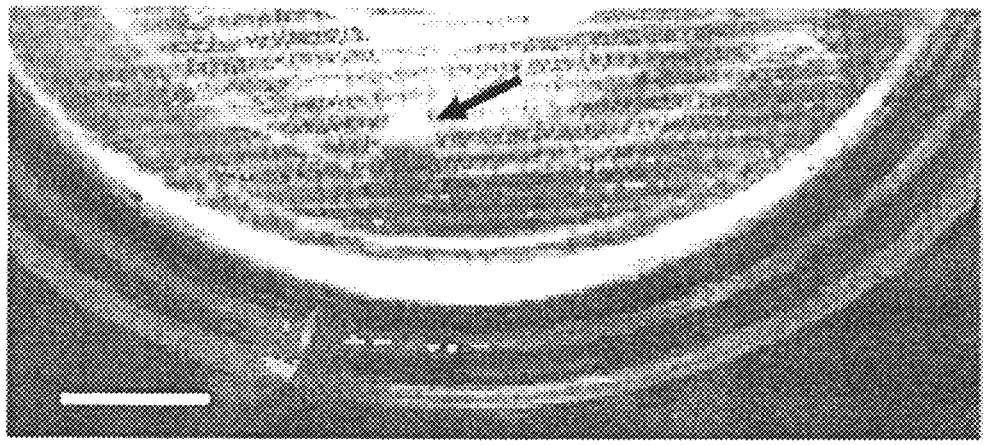
FIGS. 2A-2B present images of mineralized three-dimensional bone constructs at 14 days of mineralization (FIG. 2A) and 21 days of mineralization (FIG. 2B). The scale bars each represent 1 cm.
Figure 2B:
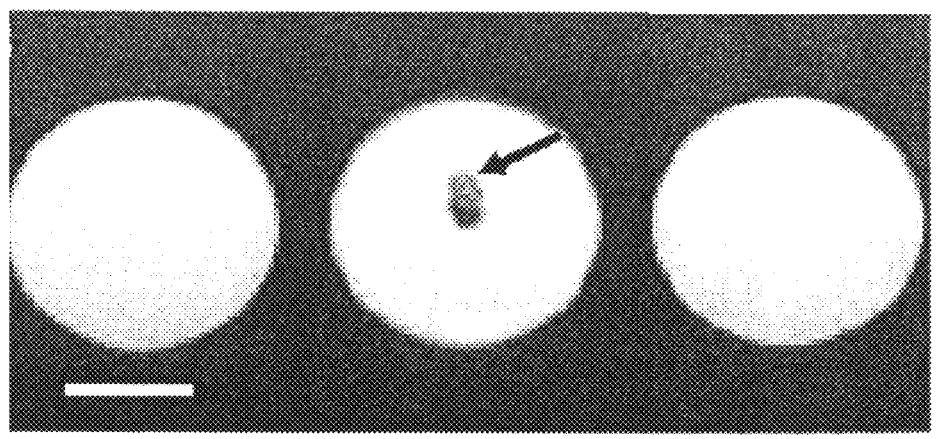

The method of Example 2 was followed, with the following differences: primary osteoblasts and osteoclast precursors were mixed together at about a 2:1 ratio of osteoblasts to osteoclast precursors, with the total number of cells being about 9 million cells; the mixture of cells was then horizontally rotated at 2 rpm for 48 hrs, and then at 14 rpm for 5 days; and mineralization proceeded at 16 rpm for 21 days. The resulting mineralized three-dimensional bone constructs are pictured in FIG. 2A (at 14 days of mineralization) and FIG. 2B (at 21 days of mineralization). The scale bar in each figure is 1 cm.

Example 4

Bone Constructs With Labeled Osteoclasts

Figure 3A:
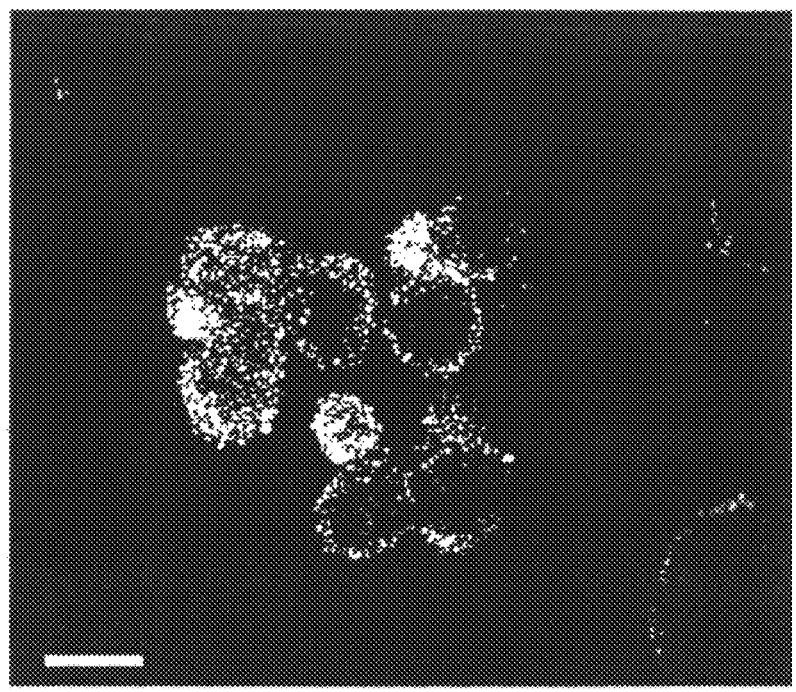
FIGS. 3A-3B present images of mineralized three-dimensional bone constructs.
Figure 3B:
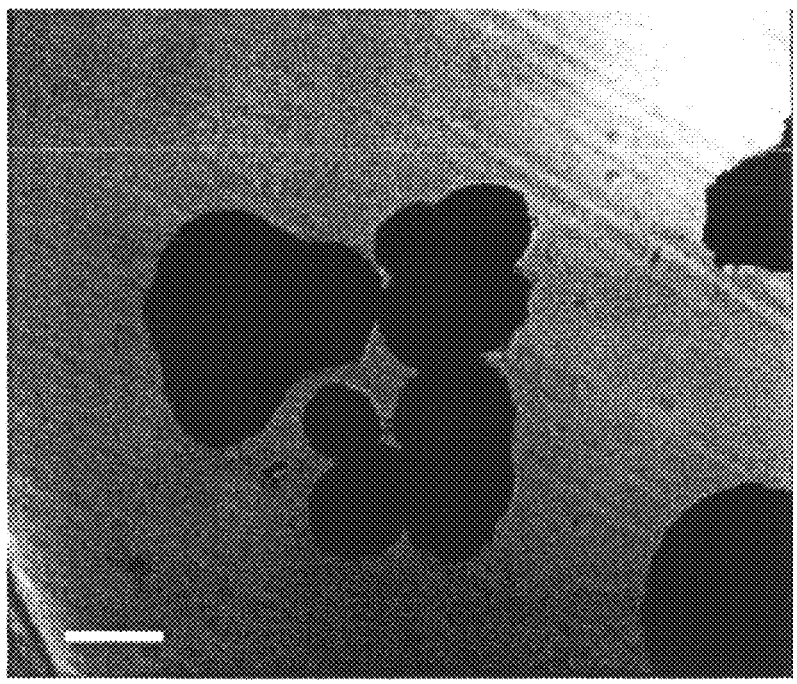

The method of Example 2 was followed, with the following differences: osteoclast precursors were labeled with the fluorescent CellTracker-Red probe (Invitrogen, Inc.) prior to mixing with osteoblasts; primary osteoblasts and labeled osteoclast precursors were mixed together at about a 2:1 ratio of osteoblasts to osteoclast precursors, with the total number of cells being about 3 million cells; the mixture of cells was then horizontally rotated at 2 rpm for 24 hrs, and then at 14 rpm for 5 days; and mineralization proceeded at 16 rpm for 14 days. FIG. 3A shows a fluorescence confocal microscopy image of an optical section through some of the resulting mineralized three-dimensional bone constructs. The results show that osteoclast precursor cells (observable as white spots in FIG. 3A) have spatially arranged themselves as an outer layer of the mineralized three-dimensional bone constructs with the putative osteoblast cells being embedded in the crystalline matrix of the central region of the constructs. FIG. 3B shows the same constructs viewed in incident laser light (i.e. non-fluorescent illumination) to illustrate the shape of the constructs. The scale bar in each of FIG. 3A and FIG. 3B is 200 µm.

Example 5

Optic Sectioning of a Bone Construct With Labeled Osteoclasts

Figure 4:
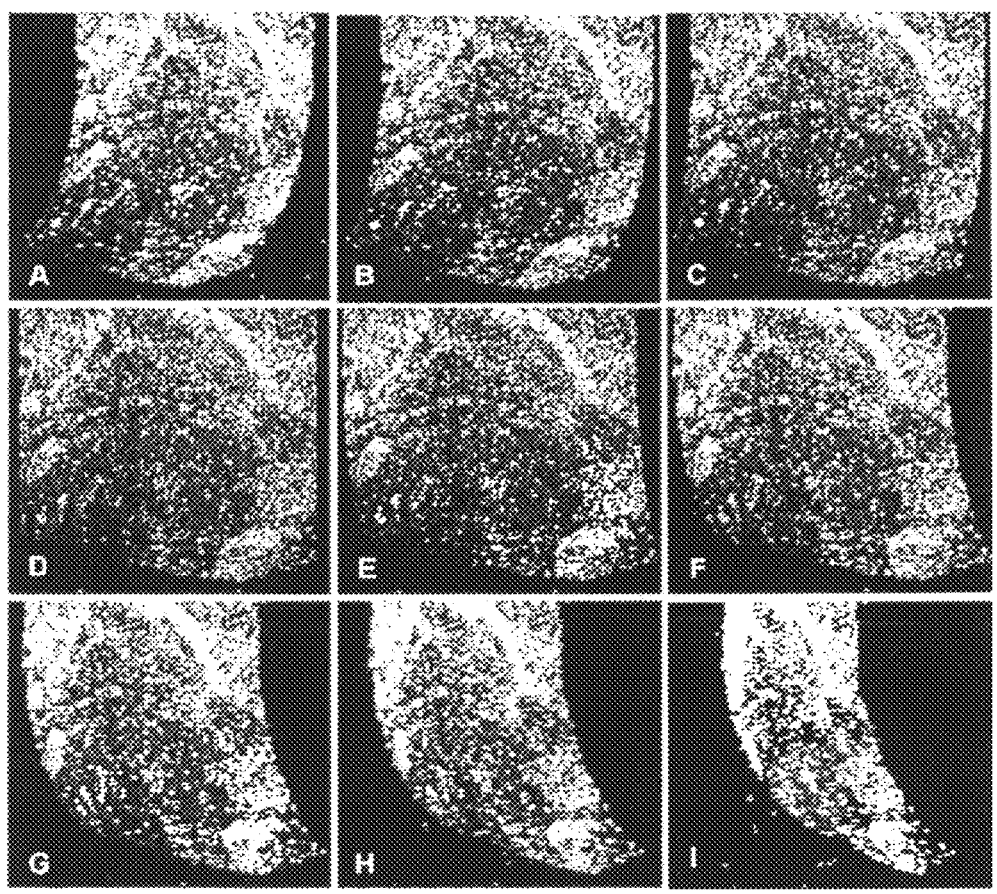
FIG. 4 presents a three dimensional reconstruction of a large bone construct using Z series confocal imaging. Osteoclast precursors were labeled with a fluoescent cell tracking dye. Panels A-I in FIG. 4 are the individual images used by the confocal imaging software to build the optical reconstruction of the bone construct in three dimensions, each image representing a sequential view over the surface of the construct (white spots indicate individual cells).

The method of Example 2 was followed, with the following differences: osteoclast precursors were labeled with the fluorescent CellTracker-Green probe (Invitrogen, Inc.) prior to mixing with osteoblasts; primary osteoblasts and labeled osteoclast precursors were mixed together at about a 2:1 ratio of osteoblasts to osteoclast precursors, with the total number of cells being about 6 million cells; the mixture of cells was then horizontally rotated at 2 rpm for 48 hrs, and then at 14 rpm for 5 days; and mineralization proceeded at 16 rpm for 21 days. Three dimensional reconstruction of a resulting large bone construct was performed using Z series confocal imaging. Panels A-I in FIG. 4 are the individual images used by the confocal imaging software to build the optical reconstruction of the bone construct in three dimensions, each image representing a sequential view over the surface of the construct (white spots indicate individual cells). FIG. 4 indicates that the arrangement of osteoclasts to the outer layer of the construct remains a feature of the construct even after extended culture periods (i.e. a total of four weeks in the HARV vessel, including three weeks grown in mineralization conditions). Labeled osteoclasts are apparent in an outer layer covering the surface of the construct.

Example 6

Figure 5B:
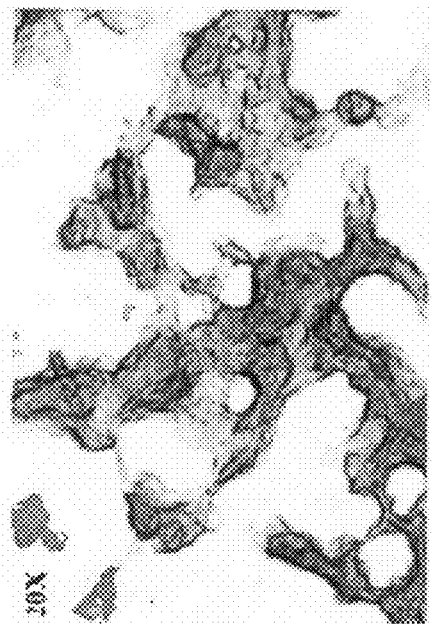
FIGS. 5A-5D show Alizarin red S staining and von Kossa staining of sections through a bone construct.
Figure 5D:
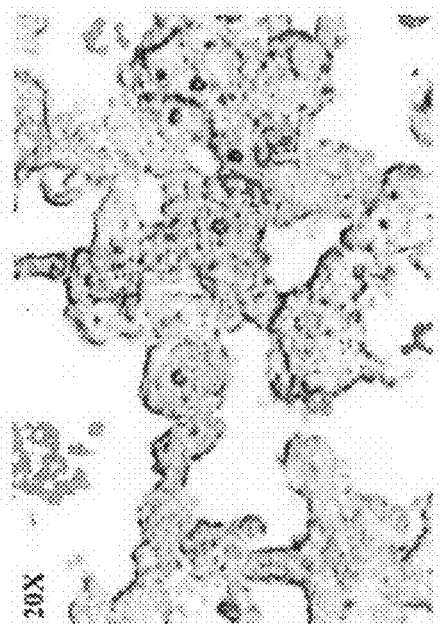
Figure 5A:
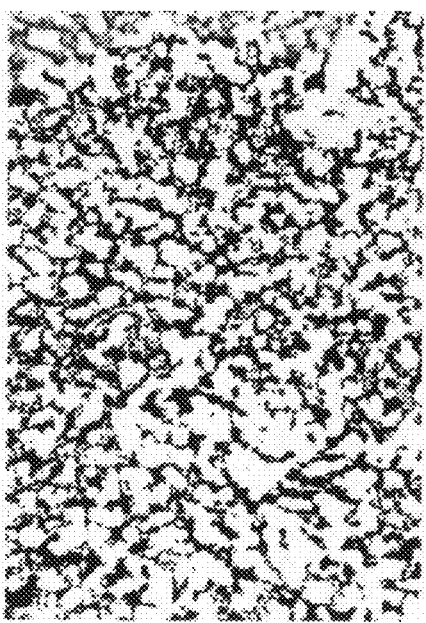
Figure 5C:
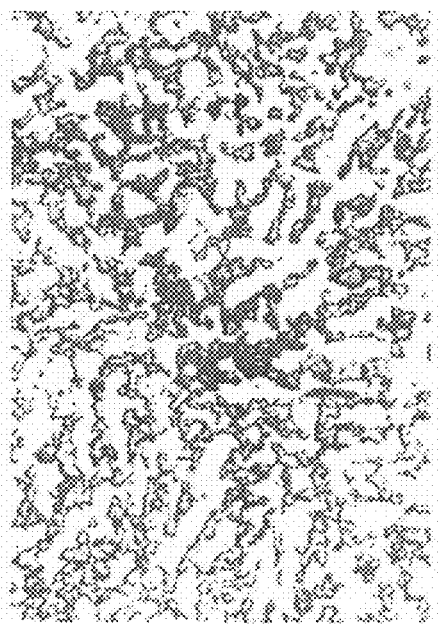

Staining of Bone Constructs With Alizarin Red S, von Kossa, and Harris Hematoxylin Stains Mineralized three-dimensional bone constructs were prepared as detailed in Example 3. The bone constructs were then fixed using a Bouin's solution (a rapid penetrating fixative solution), frozen sectioned, and stained for calcium using the Alizarin red S stain and for phosphates and carbonates using the von Kossa histochemical stain. FIG. 5A shows a 5× magnification image of Alizarin red S staining and FIG. 5B shows a 20× magnification image of Alizarin red S staining (which appears as the dark regions of the images). FIG. 5C shows a 5× magnification image of von Kossa staining and FIG. 5B shows a 20× magnification image of von Kossa staining (which appears as the dark regions of the images). The results demonstrate that the crystalline matrix of the mineralized three-dimensional bone constructs contain mineral elements observed in normal human bone in vivo.

Figure 6A:
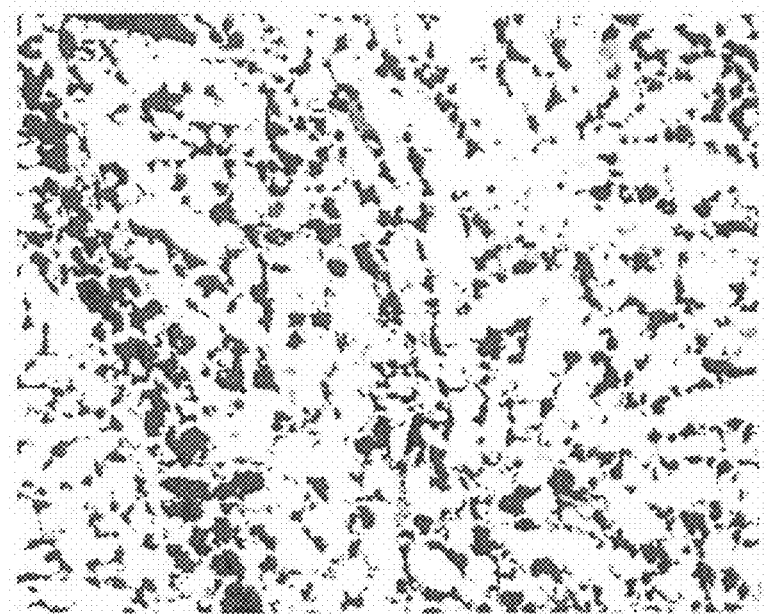
FIGS. 6A-6B show Harris Hematoxylin staining of sections through a bone construct.
Figure 6B:
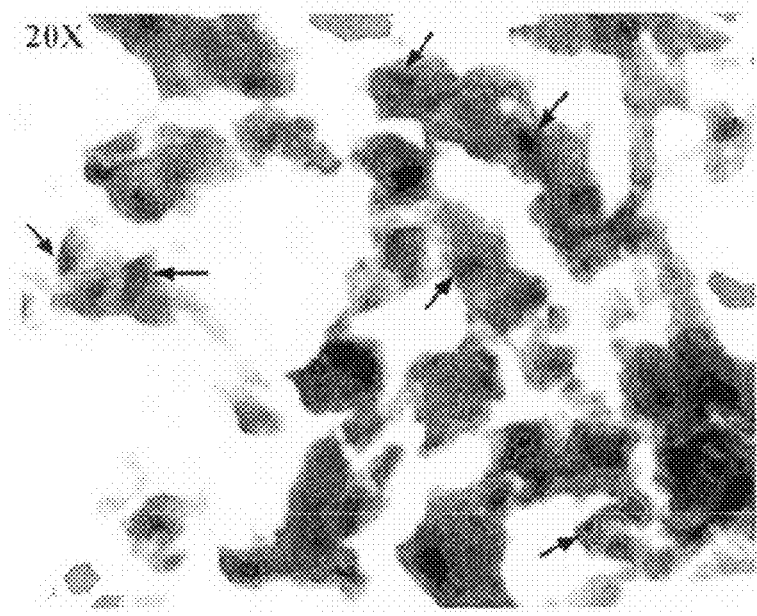

The same sections were also stained for the presence of nucleated cells using the Harris Hematoxylin stain. The results are shown in FIG. 6A (5× magnification image) and FIG. 6B (20× magnification image). The dark regions of the image indicate staining. The staining pattern illustrates a large number of cells embedded within the crystalline matrix of the three dimensional construct. These cell nuclei appear intact with little or no signs of nuclear fragmentation, a histological indicator of the occurrence of cell death/apoptosis. Arrows in FIG. 6B point to large numbers of cells embedded within the crystalline matrix in the three dimensional construct. Cell nuclei appear intact with little or no signs of nuclear fragmentation; such fragmentation would be a histological indicator of the occurrence of cell death/apoptosis. Immuno-staining of these sections for the presence of osteoblast cell markers, such as alkaline phosphatase, indicated the absence of osteoblast cell markers in the cell type embedded in the crystalline matrix. Thus, it is believed that the cells embedded in the crystalline matrix are osteocytes.

Example 7

Figure 7A:
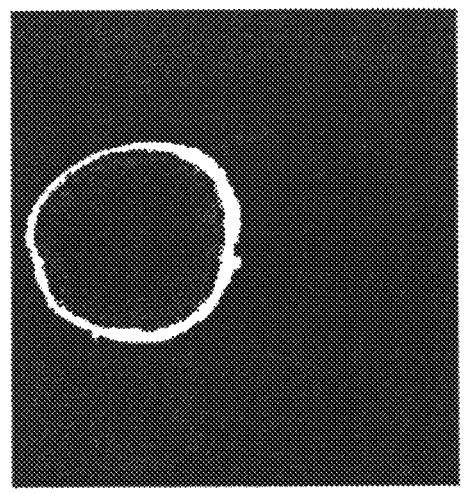
FIGS. 7A-7C show images of bone construct in which osteoclast precursors were labeled with a fluorescent cell tracking dye prior to formation of the bone construct, and the bone construct was stained with a primary antibody against osteocalcein (a marker of osteoclast differentiation) and an Alexa 488-labeled secondary antibody.
Figure 7B:
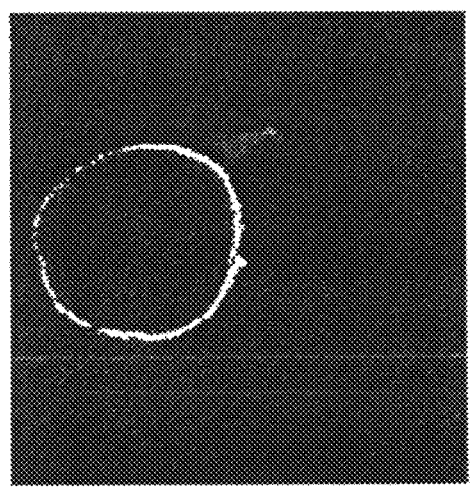
Figure 7C:
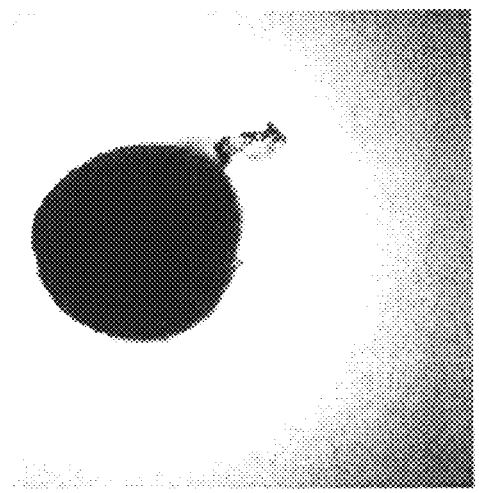

Detection of Osteocalcein, An Osteoclast Differentiation Marker, In Bone Constructs Using Immunofluorescence The method of Example 2 was followed, with the following differences: osteoclast precursors were labeled with the fluorescent CellTracker-Orange probe (Invitrogen, Inc.) prior to mixing with osteoblasts; primary osteoblasts and labeled osteoclast precursors were mixed together at about a 2:1 ratio of osteoblasts to osteoclast precursors, with the total number of cells being about 6 million cells; the mixture of cells was then horizontally rotated at 2 rpm for 48 hrs, and then at 14 rpm for 5 days; and mineralization proceeded at 16 rpm for 21 days. The resulting mineralized three-dimensional bone constructs were fixed using a phosphate buffered saline solution (pH 7.2) containing 1% (v/v) freshly generated formaldehyde. The fixed bone constructs were then immunochemically stained using a monoclonal antibody against osteocalcein (an osteoclast differentiation marker) as the primary antibody and an Alexa 488-labeled secondary antibody. FIG. 7A-7C shows images obtained by simultaneously imaging both markers in one of the bone constructs using confocal microscopy. Specifically, FIG. 7A shows osteocalcein staining, FIG. 7B shows CellTracker-Orange staining, and FIG. 7C shows the same construct illuminated with incident laser light. The results indicate that osteocalcein staining and Cell-Tracker-Orange staining (both visible as a white "ring" around the construct in FIGS. 7A and 7B) are spatially localized to the same area of the construct. This indicates that the osteoclast precursor cells had differentiated into mature osteoclasts that were spatially localized to the surface of the construct.

What is claimed is:

1. A method for promoting formation of a three-dimensional osteogenic cell aggregate ex vivo, the method comprising:
    (a) introducing osteoclast precursors and osteoblasts into a cylindrical culture vessel that rotates about a central horizontal axis,
    wherein said cylindrical culture vessel contains a matrix-free culture medium, wherein the matrix-free culture medium does not comprise an exogenous scaffolding material that guides formation of the three-dimensional osteogenic cell aggregate,
    (b) co-culturing said osteoblasts and said osteoclast precursors in said cylindrical culture vessel during horizontal rotation at a rate of between 1 and 2 rotations per minute to promote scaffold-free interaction, aggregation and organization of said osteoclast precursors and said osteoblasts until the three dimensional tissue constructs are formed,
    (c) further culturing, the tome dimensional aggregate of step (b) in a matrix-free mineralization culture medium in said cylindrical culture vessel at a higher average rate of horizontal rotation than the average rate of horizontal rotation during step (b) to increase perfusion and thereby to form mature three dimensional mineralized osteogenic cell aggregate composed of osteoblasts and osteoclasts differentiated from osteoclast precursors,
    wherein mineralized three dimensional osteogenic cell aggregate comprise an outer zone comprising osteoclasts surrounding an inner porous core comprising osteoblasts and/or osteocytes encased in a mineralized extracellular matrix.

2. The method of claim 1, wherein said cylindrical culture vessel is a High Aspect Ratio Vessel (HARV) having a diameter greater than its height 3. The method of claim 1 wherein the ratio of osteoblasts: osteoclast precursors introduced into said cylindrical culture vessel in step (a) is between about 2:1 and about 3:1.

4. The method of claim 3 wherein between about 1 million and about 8 million osteoblasts are introduced into said cylindrical culture vessel in step (a).

5. The method of claim 1 wherein rate of horizontal rotation of said cylindrical culture vessel is periodically adjusted during step (c) to counteract changes in the sedimentation velocity of said aggregates.

6. The method of claim 1, wherein step (b) is allowed to proceed for between about 5 days and about 7 days.

7. The method of claim 1. wherein step (c) is allowed to proceed for between about 7 days and about 21 days.

8. The method of claim 1, wherein said cylindrical culture vessel has a diameter of about 10 cm and a height of about 1 cm, and wherein the higher average rate of horizontal rotation than the average rate of horizontal rotation during step (b) is between about 9 revolutions per minute and about 16 revolutions per minute.

9. The method of claim 1, wherein the size of each three dimensional osteogenic cell aggregate in step (b) is between about 200 μm and about 4 mm in diameter.

10. The method according to claim 1, wherein the matrix-free culture medium of step (a) comprises at least one osteoblast differentiation factor and at least one osteoclast differentiation factor.

11. The method of claim 10, wherein said at least one osteoclast differentiation factor comprises Receptor Activator of NF-κB ligand and Macrophage Colony Stimulating Factor.

12. The method of claim 10, wherein the at least one osteoblast differentiation factor comprises ascorbic acid.

13. The method according to claim 1, wherein the matrix-free mineralization culture medium of step (c) comprises at least one osteoblast differentiation factor and at least one osteoclast differentiation factor and at least one osteoblast mineralization factor.

14. The method of claim 13, wherein said at least one osteoblast mineralization factor comprises beta-glycerophosphate and hydrocortisone-21-hemisuccinate.

* * * * *